(12) United States Patent
Chan

(10) Patent No.: US 11,793,471 B2
(45) Date of Patent: Oct. 24, 2023

(54) METHOD AND SYSTEM FOR MONITORING A DIABETES TREATMENT PLAN

(71) Applicant: Sidney Soong-Ling Chan, Singapore (SG)

(72) Inventor: Sidney Soong-Ling Chan, Singapore (SG)

(*) Notice: Subject to any disclaimer, the term of this patent is extended or adjusted under 35 U.S.C. 154(b) by 52 days.

(21) Appl. No.: 16/616,367

(22) PCT Filed: Jun. 20, 2017

(86) PCT No.: PCT/CA2017/050753
§ 371 (c)(1),
(2) Date: Nov. 22, 2019

(87) PCT Pub. No.: WO2018/232487
PCT Pub. Date: Dec. 27, 2018

(65) Prior Publication Data
US 2020/0121257 A1    Apr. 23, 2020

(51) Int. Cl.
A61B 5/00          (2006.01)
G16H 50/30        (2018.01)
(Continued)

(52) U.S. Cl.
CPC ........ A61B 5/7275 (2013.01); A61B 5/14532 (2013.01); A61B 5/4848 (2013.01);
(Continued)

(58) Field of Classification Search
CPC ... A61B 5/746; A61B 5/4848; A61B 5/14532; A61B 5/7275; G16H 20/10; G16H 50/70; G16H 50/30
(Continued)

(56) References Cited

U.S. PATENT DOCUMENTS 6,277,071 B1    8/2001  Hennessy et al.
6,421,633 B1    7/2002  Heinonen et al.
(Continued)

FOREIGN PATENT DOCUMENTS

CA    2495648        7/2014
CA    3027019 A1    12/2016
(Continued)

OTHER PUBLICATIONS

Nathan, D. M., Turgeon, H., Regan, S., "Relationship between glycated haemoglobin levels and mean glucose levels over time", Diabetologia, Nov. 2007, pp. 2239-2244, vol. 50, Issue 11, Springer-Verlag, United States of America.
(Continued)

Primary Examiner — Daniel L Cerioni
Assistant Examiner — Jonathan E. Cooper
(74) Attorney, Agent, or Firm — Spencer Fane LLP

(57) ABSTRACT

A method and system for monitoring the effectiveness of a patient's diabetes treatment plan by predicting, on a frequent basis, the patient's glycated hemoglobin (A1c) based on the patient's blood glucose (BG) may include applying a plurality of A1c models to a BG data set of the patient so as to obtain a plurality of calculated A1c values and identifying a best fit model amongst the plurality of A1c models by evaluating the plurality of calculated A1c values against at least one measured A1c value; calculating a predicted A1c value by applying the identified best fit model to the BG data set. Some embodiments may further include evaluating the predicted A1c value against a set of escalation rules to determine whether an escalation alert is required; alerting the patient's healthcare provider when it is determined the escalation alert is required; and outputting the predicted A1c value to the patient.

28 Claims, 3 Drawing Sheets

(51) Int. Cl.
- G16H 50/70 (2018.01)
- G16H 20/10 (2018.01)
- A61B 5/145 (2006.01)

(52) U.S. Cl.
CPC .............. *A61B 5/746* (2013.01); *G16H 20/10* (2018.01); *G16H 50/30* (2018.01); *G16H 50/70* (2018.01)

(58) Field of Classification Search
USPC ........................................................ 600/365
See application file for complete search history.

(56) References Cited

U.S. PATENT DOCUMENTS

| | | | |
|---|---|---|---|
| 8,538,703 B2 | 9/2013 | Kovatchev et al. | |
| 8,924,159 B2 | 12/2014 | Taub et al. | |
| 2002/0106709 A1* | 8/2002 | Potts | A61B 5/14532 435/14 |
| 2003/0212317 A1* | 11/2003 | Kovatchev | G16H 50/50 600/365 |
| 2007/0232876 A1* | 10/2007 | Otto | G16H 15/00 600/365 |
| 2009/0299151 A1* | 12/2009 | Taub | A61B 5/14546 600/300 |
| 2010/0145174 A1* | 6/2010 | Alferness | G16H 20/10 600/300 |
| 2010/0198021 A1 | 8/2010 | Alferness et al. | |
| 2010/0330598 A1 | 12/2010 | Thukral et al. | |
| 2012/0253840 A1* | 10/2012 | Murata | G16H 10/40 705/2 |
| 2012/0271557 A1* | 10/2012 | Sekimoto | A61B 5/14503 702/19 |
| 2015/0073243 A1* | 3/2015 | Taub | A61B 5/4839 600/347 |
| 2016/0004813 A1 | 1/2016 | Kovatchev et al. | |

FOREIGN PATENT DOCUMENTS

| | | |
|---|---|---|
| EP | 2486851 A1 | 8/2012 |
| WO | 2011084208 A | 7/2011 |
| WO | 2017031440 A1 | 2/2017 |

OTHER PUBLICATIONS

Nathan, D. M., Kuenen, J., Borg, R., Zheng, H., Schoenfeld, D., Heine, R. J., "Translating the A1C Assay into Estimated Average Glucose Values", Diabetes Care, Aug. 2008, pp. 1-6, vol. 31, Issue 8, American Diabetes Association, United States of America.

Nathan, D. M., Cleary, P. A., Backlund, J. C., Genuth, M., Lachin, J. M., Orchard, T. J., Raskin, P., Zinman, B.,"Intensive Diabetes Treatment and Cardiovascular Disease in Patients with Type 1 Diabetes", The New England Journal of Medicine, Dec. 22, 2005, vol. 353, Issue 25, pp. 2643-2653, United States of America.

American Diabetes Association, "Standards of Medical Care in Diabetes—2017", The Journal of Clinical and Applied Research and Education Diabetes Care, Jan. 2017, pp. 1-142, vol. 40, Supplement 1, American Diabetes Association, United States of America.

Centers for Disease Control and Prevention, "National Diabetes Fact Sheet: National estimates and general information on diabetes and prediabetes in the United States", National Diabetes Fact Sheet, 2011, pp. 1-12, U.S. Department of Health and Human Services, Centers for Disease Control and Prevention, Atlanta, GA, United States.

Khunti, K., Wolden, M. L., Thorsted, B. L., Andersen, M., Davies, M. J., "Clinical inertia in People with Type 2 Diabetes, A retrospective cohort study of more than 80,000 people", Diabetes Care, Nov. 2013, pp. 3411-3417, vol. 36, American Diabetes Association, United States of America.

Makris, K., Spanou, L., Rambaouni-Antoneli, A., Koniari, K., Drakopoulos, I., Rizos, D., Haliassos, A., "Original Article: Clinical Care and Delivery—Relationship between mean blood glucose and glycated haemoglobin in Type 2 diabetic patients", Diabetic Medicine, Feb. 2008, pp. 174-178, vol. 25, Issue 2, Diabetes UK, United Kingdom.

Rohlfing, C. L., England, J. D., Wiedmeyer, H., Tennill, A., Little, R. R., Goldstein, D. E., "Defining the Relationship Between Plasma Glucose and HbA1c", Diabetes Care, Feb. 2002, pp. 275-278, vol. 25, Issue 2, American Diabetes Association, United States of America.

Nathan, D. M., Singer, D. E., Hurxthal, K., Goodson, J. D., "The Clinical Information Value of the Glycosylated Hemoglobin Assay", The New England Journal of Medicine, Feb. 9, 1984, pp. 341-346, vol. 310, Issue 6, Massachusetts Medical Society, United States of America.

Chau, Simon, International Search Report for PCT/CA2017/050753 dated Mar. 16, 2018, 3 Pages, ISA/CA, Gatineau, Quebec, Canada.

Law, Graham R., Gilthorpe, Mark S., Secher, Anna L., Ternple, Rosemary, Bilous, Rudolf, Mathiesen, Elisabeth R., Murphy, Helen R., Scott, Eleanor M., "Translating HbA1c measurements into estimated average glucose values in pregnant women with diabetes", Diabetologia, Jan. 19, 2017, pp. 618-624, vol. 60, Issue 4, Springer, Berlin.

IP Australia, Examination Report No. 1 for Standard Patent Application, dated Jan. 25, 2023 issued in relation to the corresponding international application No. PCT/CA2017/050753 filed on Jun. 20, 2017.

IPOS Intellectual Property Office of Singapore, Search Report, dated May 12, 2021 issued in relation to the corresponding international application No. PCT/CA2017/050753 filed on Jun. 20, 2017.

European Patent Office, Supplementary European Search Report, dated Jan. 11, 2021 issued in relation to the corresponding international application No. PCT/CA2017/050753 filed on Jun. 20, 2017.

* cited by examiner

METHOD AND SYSTEM FOR MONITORING A DIABETES TREATMENT PLAN

FIELD

This disclosure relates to methods and systems for monitoring the effectiveness of a diabetes treatment plan; in particular, the present disclosure relates to such methods and systems for monitoring the effectiveness of a diabetes treatment plan based on a patient's measured blood glucose levels.

BACKGROUND

The effective management of diabetes in patients present several challenges. Many patients with diabetes mellitus typically perform self-monitoring of their own blood glucose levels in the home setting, using a portable blood glucose meter, so as to monitor the fluctuations of their blood glucose levels throughout the day, usually on a daily basis. Such testing regimes may involve pricking a finger to obtain a small amount of blood, and using a portable meter to test blood glucose levels at a given point in time. A daily testing regime might involve a measuring of fasting blood glucose when the patient first wakes in the morning before consuming any food, and then additional testing may occur at some time interval after one or more meals have been consumed during the day. Such daily blood glucose monitoring may be used by the patient and their doctor, nurse, diabetes counsellor or other healthcare provider to evaluate the effectiveness of a diabetes management or treatment program, and determine when changes to the treatment program may be required.

Although blood glucose monitoring by the patient is relatively common, the data obtained from daily blood glucose monitoring is not a good indicator of the overall average blood glucose levels of a person over a given period of time. Blood glucose levels normally fluctuate throughout the day, depending on when food or drink has been consumed, as well as other factors such as the activity or hormone levels of the patient, which may vary throughout the day. Thus, although blood glucose monitoring provides a snapshot of blood glucose levels at a particular time of the day, it is not a good indicator of the person's overall health and whether the management of their diabetes has been effective.

Glycated hemoglobin, otherwise referred to as A1c, forms when hemoglobin joins with glucose in the blood. It develops when hemoglobin, a red protein within red blood cells that carries oxygen throughout the body, joins with glucose in the blood, thus becoming glycated. A measurement of glycated hemoglobin (A1c) provides healthcare providers (HCPs) with an overall indication of what the average blood glucose levels have been over the preceding weeks or months. For example, studies have shown that A1c is an index of the average glucose over the preceding period of approximately six to eight weeks. The erythrocyte red blood cell lifespan averages approximately 120 days; thus, the level of A1c at any point in time is contributed to by all circulating erythrocytes, but is most influenced by the youngest cells rather than the older cells (having a lifespan of up to 120 days). The measurement of A1c usually involves providing a patient's blood sample to a lab for testing approximately once every three months. Although portable A1c meters are available for home use, such equipment is not widely available to or used by patients. As a result, a patient's A1c levels are typically not consistently tested in a timely manner.

Because A1c is a good indicator of the average glucose levels of the patient over the preceding period of approximately six to eight weeks prior to the date the A1c blood sample is taken, it provides useful information for diagnosing diabetes, and for determining whether adjustments to a treatment plan need to be made. For example, according to the latest guidelines, an A1c less than 5.7% indicates the patient is non-diabetic; an A1c between 5.7% and 6.4% indicates the patient is pre-diabetic, or at risk of developing diabetes; and an A1c above 6.5% indicates the patient is diabetic. (See Diabetes Care Volume 40, Supplement 1, January 2017, pp. s13-s16). Furthermore, the higher a patient's A1c levels are (above 7.0%), the greater the risk for that patient to develop complications relating to diabetes.

According to the American Diabetes Association, escalation of treatment options follows general guidelines; for example, if the patient is using one non-insulin diabetes therapy, whether oral or injectable, and fails to meet an A1c target as determined by the HCP and the patient within three months, then the recommendation is to intensify treatment to either two non-insulin therapies or to commence administration of basal insulin. Similarly, where patient is using two non-insulin therapies and fails to meet the A1c target agreed to between the patient and the HCP within a period of three months, the guidelines recommend treatment escalation to either three non-insulin therapies or to commence administration of basal insulin. For patients using three non-insulin therapies who fail to meet the A1c target within three months, the recommendation of the guidelines is to commence administration of basal insulin.

The problem is that there is a general failure, by HCPs and patients, to adhere to the ADA guidelines regarding escalation of treatment, leading to an increase in diabetes complications which could otherwise be avoided if treatment escalation or other intervention occurred in accordance with the guidelines. On the other hand, improved glycemic control may reduce the complications that arise from diabetes. Studies have shown, for example, that every percentage point drop in A1c blood test results (for example, from 8.0% to 7.0%) can reduce the risk of microvascular complications (eye, kidney and nerve diseases) by 40% (see: Centers for Disease Control and Prevention. *National diabetes fact sheet: national estimates and general information on diabetes and prediabetes in the United States*, Atlanta, Ga.: U.S. Department of Health and Human Services, Centers for Disease Control and Prevention, 2011.)

The pervasiveness of the problem of not escalating diabetes treatment in response to elevated A1c has been documented. For example, one study involving more than 80,000 diabetes patients (K. Khunti et al, "Clinical Inertia in People with Type 2 Diabetes", Diabetes Care, Vol. 36, November 2013, p. 3411) shows that for patients having an A1c level of 8.7% or more, the average length of time it took to escalate therapy from a single non-insulin therapy to dual non-insulin therapies was 19 months, rather than the recommended three months found in the ADA guidelines. For patients having an A1c level of 8.8% or above, it took an average of 82 months to escalate from dual non-insulin therapy to triple non-insulin therapy, a significantly longer period of time than the recommended three months in the ADA guidelines. In the same study, it was found that patients requiring escalation to basal insulin were not prescribed that escalation for a number of years. For example, patients having an average of 9.4% A1c and taking one non-insulin therapy took an average of 6.9 years to be escalated to basal insulin. It also took 6.9 years, on average, to escalate treatment to basal insulin for patients having A1c levels of 9.8% and on dual non-insulin therapy. For patients having an average of 9.7% A1c taking three non-insulin therapies, it took an average of six years to escalate treatment to basal insulin. According to the ADA guidelines, patients having over 9% A1c should be immediately prescribed basal insulin in order to bring their diabetes under effective control.

It has been previously proposed that correlating average blood glucose levels to the patient's A1c levels may assist with more effective monitoring of the patient's overall control of their diabetes. Several different studies have suggested various different models for correlating average blood glucose to the patient's A1c levels. However, to the applicant's knowledge, no single model has been found to date that is able to accurately correlate the blood glucose levels and A1c values of all patients who have diabetes. This is due in part to the fact that there are many different variables which may impact the blood glucose levels of a patient and the overall index value of a patient's blood glucose over a period of time, as provided by the A1c measurement. Such factors include not only the frequency and specific timing of blood glucose measurements obtained by the patient through self-monitoring, as well as various other physiological and lifestyle factors which may differently impact each patient. A further issue with the effective use of daily blood glucose monitoring to determine when intervention in a diabetes management treatment plan may be required is that the patient may not be consistent about transmitting such data to their HCP in a timely matter, and in addition, the HCP may lack the time and other resources to perform the necessary calculations, even when a complete blood glucose data set of a given patient is available.

In U.S. Pat. No. 8,924,159 by Taub et al, (the '159 patent), there is described a method and apparatus for providing glycemic control of a patient. In some aspects of the method and apparatus described in the '159 patent, it is suggested that continuously monitored blood glucose measurements produces data which may be more accurately correlated to a patient's A1c levels, as compared to self-monitored blood glucose measurements taken at certain intervals throughout the day. Continuously monitored glucose measurements typically involve inserting a probe or sensor underneath the patient's skin, which probe continuously monitors blood glucose levels at a given interval, for example every 10 minutes, and then the probe transmits the blood glucose data to a receiver. Thus, continuously monitored glucose measurements require more sophisticated equipment than what is generally used for the more typical method of self-monitoring blood glucose meters, which involve taking a given number of measurements, for example one, four or seven measurements in a day, by pricking the finger and using a test strip to receive a blood sample and then inserting the strip into the monitor.

In U.S. Pat. No. 8,538,703 issued to Kovatchev et al (the '703 patent), a method, system, and computer program product related to the maintenance of optimal control of diabetes is described. The method and system described in the '703 patent includes predicting the long-term exposure to hyperglycemia in the long-term, and short-term risks of severe or moderate hypoglycemia in diabetics based on blood glucose readings collected by a self-monitoring blood glucose device. In one aspect of the '703 patent, it is described that the calculation of A1c is based upon a predetermined period of collected self-monitoring blood glucose data, for example over a period of 4 to 6 weeks. The estimation of A1c utilizes at least one of four predetermined formulas and validation of the estimate through sample selection criteria is also performed. The mathematical equations applied to predict A1c depend, in part, on the time of day that the readings are taken. The method and system described in '703 patent further includes prediction of the long-term risk of a severe hypoglycemia event occurring within the next six months, and an estimated short-term risk of a hypoglycemia event occurring within the next 24 hours, and further suggests enhancement of emerging continuous monitoring devices having these same features.

In US patent publication number 2010/0330598 by Thukral et al (the '598 patent publication), a method and system for providing both an estimated true mean blood glucose value and estimated glycated hemoglobin (A1c) value from data obtained from blood glucose monitoring is disclosed. The blood glucose measurements and associated context of the blood glucose measurements are collected daily at times specified by a structured sampling schema, and the collected blood glucose measurements are weighted based on the associated context. The estimated true mean blood glucose value and the estimated A1c value are then determined from the weighted blood glucose measurements over a period of one day. A computer program for implementing the method for providing both an estimated true mean blood glucose value and estimated glycated hemoglobin value from spot blood glucose measurements is also disclosed. In an example embodiment disclosed in the '598 publication, the patient is required to input event information concerning the patient's lifestyle in addition to the blood glucose measurement itself. Such information includes whether the patient has had breakfast, lunch, supper, a snack, some exercise or physical activity, stress, and optionally any other relevant information that may be provided for in the blood glucose meter. The '598 patent publication relies on the use of a structured sampling scheme for discounting the individual physiology variations of a given patient and the impact that has on a patient's A1c and its correlation to self-monitored blood glucose values.

In international patent publication number WO 2011/084208 by inventor Murata (the '208 patent publication), a system and method for estimating A1c, diabetic patient treatment response, and hypoglycemia risk using data obtained from patient self-monitoring of blood glucose is provided. In the '208 patent publication, instead of calculating an arithmetic mean, an embodiment uses time weighted glucose averages at selected points in the day to obtain a projected A1c for a specific set of glucose readings. The method disclosed in the '208 patent publication requires a seven point daily blood glucose profile, wherein patients are required to self monitor their blood glucose levels seven times per day, including for example before breakfast, before lunch, before dinner, and at bedtime. Additional measurements are required two hours after breakfast, two hours after lunch, and/or two hours after dinner. A1c may be calculated by two independent methods; one based upon the area under a glucose concentration time curve and the other based upon multiple linear model. In other aspects, the patient's HCP may specify a time interval of interest in selecting from among a seven-point, four-point, two-point, or one-point glucose profile. As with the '598 patent publication, the '208 patent publication describes assigning different weights to the different blood glucose measurements taken throughout the day, according to the contribution of each of those measurements to the determination of the A1c levels of the patient.

SUMMARY

A system and method is provided herein for using a patient's daily blood glucose measurements to predict the patient's present A1c levels, which information may be used by the patient and the HCP to monitor the effectiveness of the patient's diabetes management program. In some aspects of the present disclosure, the patient's predicted A1c, based on data obtained from daily blood glucose monitoring, may be provided to the HCP on a frequent basis, and the system may further include automated alerts to the HCP and/or automated scheduling of follow-up appointments between the HCP and the patient whenever the predicted A1c values indicate that escalation of the treatment plan may be required.

Advantageously, in some aspects of the present disclosure, the systems and methods disclosed herein predict a patient's A1c levels based on data obtained from self-monitoring of the patient's blood glucose levels. This is done without requiring a particular testing regime which may be difficult for a patient to adhere to on a consistent basis, and without requiring continuous blood glucose monitoring, a testing technology which may be more expensive than a traditional blood glucose monitor and which may be considered to be invasive by some patients.

Numerous studies have previously attempted to derive a mathematical relationship or correlation between a person's average daily blood glucose levels calculated over a proceeding period of time and the person's A1c levels. While several of these previous attempts show that there is likely some mathematical correlation between a person's average blood glucose levels and their A1c levels, the general consensus is that no one formula is able to reproducibly predict every individual patient's A1c levels based on their average blood glucose levels, due to the many variables that may impact an individual patient's blood glucose and A1c levels including their lifestyle and physiology, amongst other factors. The applicant has determined, however, that most patients' blood glucose data may have a high level of correlation with A1c based on any one of the numerous mathematical formulas or models that have been previously discovered or identified by others. From time to time, a particular patient's blood glucose data may better correlate with a different mathematical formula than one that was previously identified as a best fit model at a given point in time. Thus, the applicant uses a number of mathematical formulas or models simultaneously to calculate a plurality of A1c levels at a given point in time, based on the patient's most recent blood glucose monitoring data and running averages of those blood glucose levels over varying intervals of time. The plurality of calculated A1c values may then be compared against measured A1c values to identify which mathematical model provides the best fit for that particular patient's data at a particular point in time. The best fit mathematical formula or model may then be used to calculate the patient's predicted A1c levels on a continuing basis, and the predicted A1c levels may be continuously recalculated and updated as new blood glucose data and new A1c measurements become available.

In other aspects of the present disclosure, in addition to using a number of mathematical models to predict a person's A1c levels, it has also been found that calculating a person's average blood glucose over a selected time interval from amongst a plurality of time intervals, for example over time intervals of 15, 30, 60 and/or 90 days, may further provide for a better fit with one of the plurality of formulas or models for correlating average blood glucose and a patient's A1c levels, depending on the individual patient. By using multiple running day averages for a person's blood glucose data as well as testing a number of the different mathematical formulas to determine which combination of average blood glucose time interval and formula best fits a particular patient's blood glucose data, the applicant has found that a person's A1c levels may be predicted with a reasonable level of certainty, thereby providing the patient and the patient's HCP with useful, up-to-date information correlating the patient's latest blood glucose data and the patient's A1c levels at a given point in time. This information may usefully assist the patient and the patient's HCP in knowing whether a particular treatment plan for managing the patient's diabetes is working or needs adjustment, and this improved feedback mechanism may thereby encourage the patient to make better decisions with respect to diet, exercise, and other factors which are within the individual's control. Furthermore, advantageously the HCP may be provided with up-to-date predictions of a patient's A1c levels, which may enable the HCP to intervene earlier when the patient's blood glucose data is indicating, through the systems and methods described herein, that the patient's A1c levels are trending in a direction which indicates that treatment escalation or modification may be required.

To summarize, in one aspect of the present disclosure, a method is provided for monitoring the effectiveness of a patient's diabetes treatment plan by predicting, on a frequent basis, a patient's A1c based on the patient's blood glucose, where the method may include applying a plurality of A1c models to a blood glucose data set of the patient so as to obtain a plurality of calculated A1c values and identifying a best fit model amongst the plurality of A1c models by evaluating the plurality of calculated A1c values against at least one measured A1c value; calculating a predicted A1c value by applying the identified best fit model to the blood glucose data set. In other aspects of the present disclosure, the method further includes: evaluating the predicted A1c value against a set of escalation rules to determine whether an escalation alert is required; alerting the patient's HCP when it is determined the escalation alert is required. The predicted A1c value may also be provided to one or more other authorized persons. In some embodiments, the step of identifying the best fit model further includes determining an adjustment factor so as to adjust the best fit model to better correlate with the patient's blood glucose data set and the step of calculating the predicted A1c value further includes applying the adjustment factor to the best fit model.

DETAILED DESCRIPTION

Figure 1:
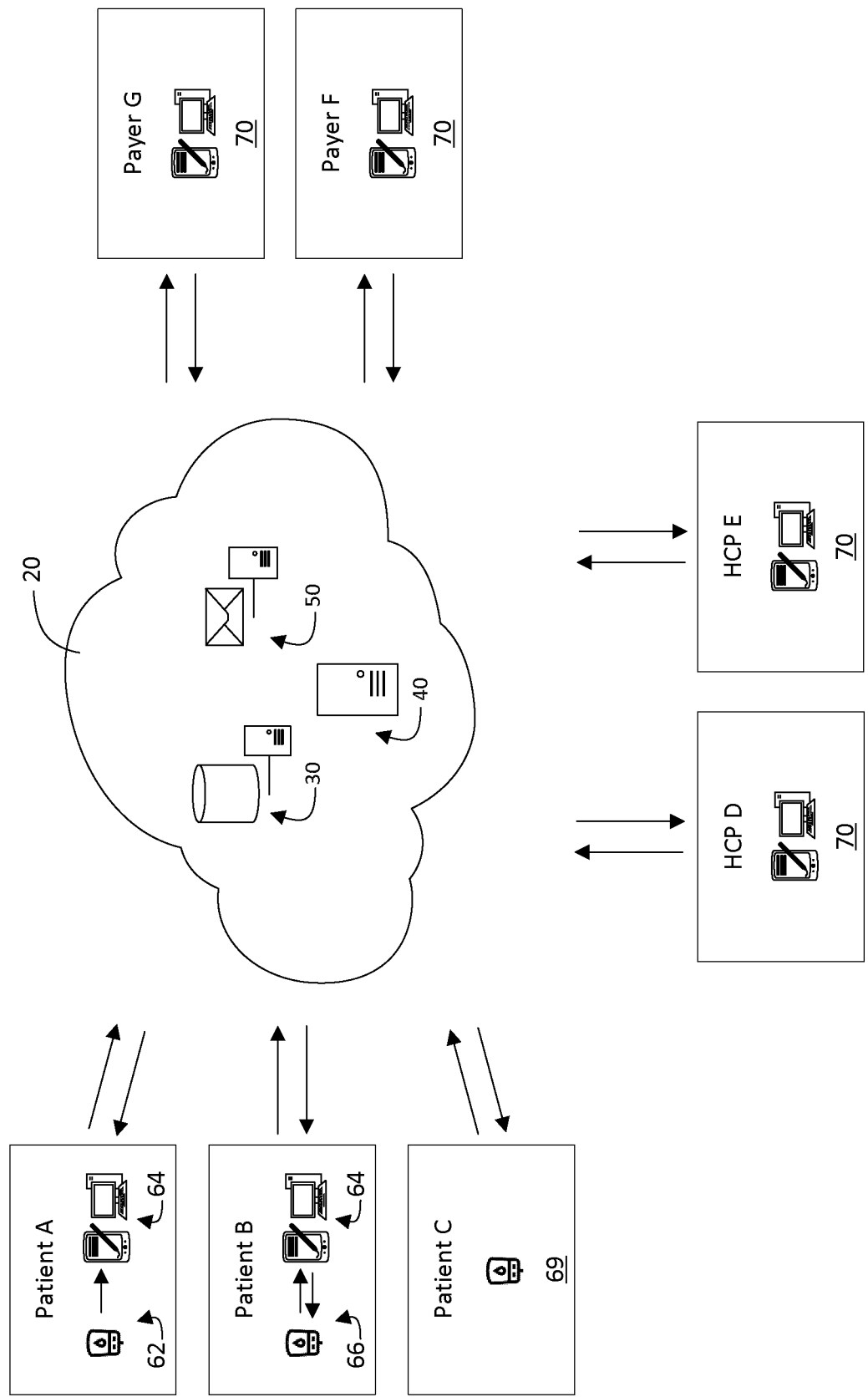
FIG. 1 is a diagrammatic view of a cloud-based platform system, in an embodiment of the present disclosure.

The present disclosure describes systems and methods which utilize blood glucose data, which may be collected by the patient, to predict the patient's A1c levels. That information may then be utilized in the monitoring of the overall effectiveness of the patient's diabetes treatment plan. Advantageously, in some aspects, this monitoring may enable the patient's HCP to intervene and make modifications to the patient's diabetes treatment plan when required. Additionally, the system and methods described herein may utilize blood glucose data collected by blood glucose meters that are presently in use, and may be configured to be capable of receiving blood glucose data from any of the portable blood glucose meters presently available in the market; as such, there may be no need to deploy specialized blood glucose meters or equipment to practice the methods and systems described herein.

As a further advantage, in some aspects of the present disclosure, the system and methods described herein do not depend on employing a particular blood glucose sampling regime, nor do the systems and methods herein described require the patient to modify the schedule or manner in which they self-monitor their blood glucose levels.

Diabetic patients, and in particular those who are taking insulin as part of their diabetes management regime, are typically instructed by their HCPs to monitor their blood glucose levels on a daily basis, sometimes once per day, or in other cases, several times per day. Patients may typically measure their own blood glucose levels by using a portable blood glucose meter, which may utilize a disposable strip which receives a small sample of blood from the patient, for example through a pinprick of the patient's finger, and this disposable strip receiving the blood sample is then inserted into the portable blood glucose meter for analysis to determine the blood glucose level at the time the sample is taken. Such daily blood glucose monitoring is typically used by patients to keep track of their own blood glucose levels, thereby informing the patient of when their blood glucose levels are spiking, potentially indicating that an action needs to be taken, such as injecting insulin in the case of a hyperglycemic event. The opposite condition, of hypoglycemia, may also occur, for example where the patient does not have sufficient blood glucose levels in their system, indicating that the patient needs to ingest sugar so as to increase their blood glucose levels. Thus, daily blood glucose monitoring is a useful tool for managing a patient's blood glucose levels throughout the day, as a patient's blood glucose levels will normally fluctuate throughout the day as a result of ingesting food, and may also be impacted by other activities such as physical activity, sleeping, fasting, hormonal fluctuations and other activities that may occur throughout the day which impact blood glucose levels of the patient.

Although useful for tracking the daily fluctuations of blood glucose in a patient, daily blood glucose monitoring does not provide a good indication of the overall management of the patient's blood glucose levels over a longer period of time. Such information is important for an HCP in making decisions about whether a patient's diabetes management program needs to be modified in some way. Thus, a measurement of the patient's A1c levels is used as a tool to provide an overall picture of the patient's management of their blood glucose levels over a period of approximately 12 weeks prior to the measurement of the patient's glycated hemoglobin levels. Decisions about whether a treatment plan needs to be modified are based on a measurement of the patient's average blood glucose levels over a period of time, as indicated by the patient's A1c levels, which is typically measured by testing an assay in a lab.

Guidelines which provide recommendations for adjusting a diabetes management plan are based on the patient's A1c levels, rather than daily blood glucose monitoring. As an individual's A1c levels increase beyond an optimal range of 6.5% to 7.0%, such increases indicate that an adjustment to the patient's diabetes management plan may be required in order to bring the patient's glucose levels under control. Additionally, an HCP in consultation with the patient may often set A1c target levels for the patient to reach, thereby providing a further measure of the effectiveness of an adjustment to a diabetes treatment plan, and the patient's adherence to that plan. For these reasons, it would be helpful for patients to have access to frequent updates about their A1c levels; however, patients normally would not have access to frequently updated A1c levels because the A1c test may typically be performed in labs and on an infrequent basis, for example, at a frequency of once every three months.

Given the importance of having up-to-date information on A1c levels as they relate to a patient's average blood glucose levels, several attempts have been made in the past by researchers to derive formulas which correlate a patient's A1c levels to their average glucose levels. Examples of these studies, and the resulting formulas or mathematical relationships discovered through these studies, will be described in further detail below. However, to the Applicant's knowledge, there is not a single formula or equation that can accurately predict all patients' A1c levels based upon their average glucose levels, as determined by daily blood glucose monitoring.

There may be several reasons for this. One reason is that the various different studies that have attempted to correlate blood glucose levels to A1c levels have involved different design studies with variances between the daily blood glucose testing regimes, as well as other variances which may impact the resulting formula. Furthermore, individual factors which vary between different patients, such as lifestyle factors, physiological factors and other variables, make it difficult to identify a single formula or model which could accurately correlate every diabetic patient's average blood glucose levels to their A1c levels. A further challenge is that there are many different recommendations for daily blood glucose testing recommended by HCPs, depending on the needs of the particular patient and the lifestyle factors that may impact the patient's ability to consistently follow a particular testing regime.

Advantageously, in one aspect of the present disclosure, the Applicant has discovered a method for using a patient's daily blood glucose monitoring data to predict that patient's A1c levels with a reasonable degree of certainty and without requiring the patient to adhere to a particular blood glucose testing regime. The method includes analysing a patient's blood glucose data and comparing calculated A1c values from that blood glucose data against that patient's A1c levels measured by a lab, to identify a best fit model which correlates the patient's average blood glucose and A1c levels with a reasonable degree of accuracy. In some aspects of the present disclosure, the identification of a best fit model for a given patient's blood glucose data may be updated as required, whenever new, updated A1c measurements performed by a lab become available. In this manner, both the patient and his or her HCP may be provided with up-to-date information about the patient's A1c levels, without requiring additional lab testing of A1c levels beyond what would normally be recommended.

Advantageously, in some aspects of the present disclosure, the systems and methods described herein may provide the HCP with continually updated information and monitoring which allows the HCP to proactively make adjustments to the patient's diabetes treatment program, and importantly, to make adjustments to the treatment program whenever an increase in the patient's A1c levels indicates that such intervention may be required. As a result, the Applicant believes that an overall reduction in the occurrence of diabetes-related complications may be achieved through the methods and systems described herein, which advantageously may not require a capital investment, by the patient or healthcare payer, in additional equipment or devices beyond the portable blood glucose meters that are already used by diabetes patients to perform self-monitoring of their blood glucose levels.

Models For Correlating Average Blood Glucose $BG_{avg}$) and Glycated Hemoglobin (A1c)

Various studies have previously derived various mathematical relationships between a patient's average blood glucose levels, as calculated from blood glucose monitoring data, and the patient's A1c. Herein, the Applicant utilizes a number of these mathematical relationships, or formulas, and incorporates those formulas into a plurality of possible models that may be used in the methods and systems described herein. The methods and systems described herein identify a best fit model for correlating or predicting a patient's average blood glucose and A1c levels. Several of these studies, and their corresponding formulas, will be briefly described below; however, it will be appreciated by persons skilled in the art that other formulas or mathematical relationships between average blood glucose levels and A1c levels, which are either presently known or which may become known in the future, may also be deployed in the methods and systems described herein, and that the present disclosure is not intended to be limited to the particular formulas and mathematical relationships described below.

In one study performed by Makris et al (K. Makris, L. Spanou, A. Rambaouni-Antoneli, K. Koniari, I. Drakopoulos, D. Rizos and A. Haliassos, "Relationship between mean blood glucose and glycated haemoglobin in Type 2 diabetic patients", Diabetic Medicine 25(2), February 2008, pp. 174-178), the authors followed 140 patients having type II diabetes. Mean blood glucose was calculated for each patient from self-measurements of blood glucose using a portable glucometer, made six times a day (before eating and two hours after a meal), three times a week for one month. A1c was determined by high performance liquid chromatography at zero weeks and at twelve weeks. The following linear relationship, correlating mean blood glucose ($BG_{avg}$), measured in units of mg/dL, with A1c:

$$BG_{avg}=34.74(A1c)-79.21$$

Rearranging the equation provides the following formula for calculating A1c from a mean, or average, blood glucose measurement ($BG_{avg}$):

$$A1c=(BG_{avg}+79.21)/34.74$$

In another study, performed by Nathan et al (D. M. Nathan, J. Kuenen, R. Borg, H. Zheng, D. Schoenfeld, R. J. Heine, "Translating the A1C Assay into Estimated Average Glucose Values," Diabetes Care, Volume 31, Number 8, August 2008) (hereinafter, "Nathan 2008"), a total of 507 subjects, including 268 patients with type I diabetes, 159 with type II diabetes, and 80 nondiabetic subjects were included in an analysis to estimate average blood glucose values from an A1c assay. A1c levels obtained at the end of three months and measured in a central laboratory were compared with the average blood glucose ($BG_{avg}$) levels during the previous three months. $BG_{avg}$ was calculated by combining weighted results from at least two days of continuous glucose monitoring performed four times, with seven-point daily self-monitoring of capillary (fingerstick) glucose performed at least three days per week. The following linear relationship, correlating $BG_{avg}$, measured in units of mg/dL, with A1c, was found:

$$BG_{avg}=28.7(A1c)-46.7$$

Rearranging the equation provides the following formula for calculating A1c from the $BG_{avg}$:

$$A1c=(BG_{avg}+46.7)/28.7$$

In the same Nathan 2008 study, an alternative linear relationship was derived, based only on $BG_{avg}$ calculated from the blood glucose data obtained from continuous interstitial glucose monitoring, which, in the study, measured glucose levels every five minutes and was performed for at least two days at baseline and then every four weeks during the next twelve months. That linear regression analysis resulted in the following linear relationship correlating $BG_{avg}$, measured in units of mg/dL, with A1c:

$$BG_{avg}=28.0(A1c)-36.9$$

Rearranging the equation provides the following formula for calculating A1c from the $BG_{avg}$:

$$A1c=(BG_{avg}+36.9)/28.0$$

In an earlier study, performed by Nathan et al (D. M. Nathan, H. Turgeon, S. Regan, "Relationship between glycated haemoglobin levels and mean glucose levels over time," Diabetologia, November 2007, Volume 50, Issue 11, pp 2239-2244) (hereinafter, "Nathan 2007"), data obtained from twenty-two participants with diabetes and three non-diabetic participants was used in this longitudinal observational study to derive a relationship between mean blood glucose levels and A1c values. For the purposes of this study, mean blood glucose levels were measured by continuous glucose monitoring, which measures interstitial glucose levels every five minutes, for twelve weeks. Capillary measurements were obtained four times per day to confirm the accuracy of the continuous glucose monitoring. A1c was measured at baseline and every 4 weeks. The following linear relationship, correlating $BG_{avg}$, measured in units of mg/dL, with A1c, was found:

$$BG_{avg}=31.5(A1c)-68.6$$

Rearranging the equation provides the following formula for calculating A1c from the $BG_{avg}$:

$$A1c=(BG_{avg}+68.6)/31.5$$

In a paper by Rohlfing et al (C. L. Rohlfing, J. D. England, H. Wiedmeyer, A. Tennill, R. R. Little, D. E. Goldstein, "Defining the Relationship Between Plasma Glucose and HbA1c," Diabetes Care, Vol. 25, No. 2, February 2002), the authors performed a linear regression analysis on the data obtained in the Diabetes Control and Complications Trial (DCCT), published in 1993. The DCCT was a multicenter, randomized clinical trial designed to compare intensive and conventional therapies and their relative effects on the development and progression of diabetic complications in patients with type 1 diabetes. Quarterly A1c and corresponding seven-point capillary blood glucose profiles (premeal, postmeal, and bedtime) obtained in the DCCT were analyzed to define the relationship between A1c and plasma glucose. Only data from complete profiles with corresponding A1c were used (n=26,056). Of the 1,441 subjects who participated in the study, two were excluded due to missing data. Linear regression analysis weighted by the number of observations per subject was used to correlate $BG_{avg}$ and A1c. The following linear relationship, correlating MPG, measured in units of mg/dL, with A1c, was found:

$$BG_{avg}=35.6(A1c)-77.3$$

Rearranging the equation provides the following formula for calculating A1c from the $BG_{avg}$:

$$A1c=(BG_{avg}+77.3)/35.6$$

In an earlier paper by Nathan et al (D. M. Nathan, D. E. Singer, K. Hurxthal, J. D. Goodson, "The Clinical Information Value of the Glycosylated Hemoglobin Assay", The New England Journal of Medicine, Vol. 310, No. 6, pp. 341-346), blood glucose and A1c data was collected from 21 patients with diabetes, who performed at least four blood glucose self-monitoring tests per day, and an A1c assay was taken at the end of the two-month period. Approximately half of the measurements were obtained 90 minutes after a meal. The following linear regression equation was generated from the calculated mean blood glucose concentration ($BG_{avg}$) and the measured A1c:

$$BG_{avg}=33.3(A1c)-86$$

Rearranging the equation provides the following formula for calculating A1c from the $BG_{avg}$:

$$A1c=(BG_{avg}+86.0)/33.3$$

Prediction of A1c Based on Blood Glucose Data

An example of how the computer implemented methods and systems, as disclosed herein, may be used to monitor the effectiveness of a patient's diabetes management plan will now be described, with reference to calculations performed on actual blood glucose data obtained from a diabetic patient. The methods and systems disclosed herein essentially involve the collection of blood glucose data by patient, typically on a daily basis, and continually providing that blood glucose data, at regular intervals, to a system, such as a cloud-based platform 20, which will include the database and processors as described above with reference to FIG. 1. Although blood glucose measurements are typically taken by a patient daily, the Applicant notes that the methods and systems disclosed herein may also work on blood glucose data sets in which the blood glucose measurements are not taken on a daily basis.

The cloud-based platform 20 then performs various calculations on the collected blood glucose data and on the measured A1c levels of the patient as determined by prior lab analysis, so as to identify a best fit model which best describes that particular patient's blood glucose data in relation to the patient's A1c levels. The system then uses the identified best fit model to continually update a predicted value of the A1c of the patient, based on the blood glucose data collected. In one aspect of the present disclosure, whenever a new A1c measurement becomes available, such as when a new lab analysis is conducted, the system may use that new measured A1c value to re-evaluate the possible mathematical models and determine which model is the best fit for the patient's data, in light of the new A1c measurement and any newly available blood glucose monitoring data, and thereby updating the best fit model based on the latest available data of the patient.

Without intending to be limiting, one embodiment of the method may include uploading the available blood glucose data for a particular patient, including any A1c measurements that have been taken in the past, to the system. For example, as provided in FIG. 3, a patient has had blood glucose data taken over a period of 90 days, wherein the blood glucose data set includes measurements taken each day for the 90 day period, with the frequency of measurements ranging from one to six measurements in a day.

In addition to the daily blood glucose data taken over a period of 90 days, the patient in this example also had three measurements of their A1c values taken over the same 90-day period. In this example, the blood glucose data was taken between Jan. 1, 2016 and Sep. 22, 2016, and the patient's A1c measurements were performed in the lab on blood samples taken on Jan. 15, 2016; May 21, 2016; and Sep. 17, 2016 (see Table 1, below.)

TABLE 1

Measured A1c Values

| Date | Measured A1c |
|---|---|
| Jan. 15, 2016 | 7.4 |
| May 21, 2016 | 8.3 |
| Sep. 17, 2016 | 7.3 |

Once the blood glucose data taken over an interval of time is available, the method provides for calculating average blood glucose levels of the patient over different periods or intervals of time. For example, without intending to be limiting, such time intervals may include periods of 15 days, 30 days, 60 days, and 90 days. In some aspects of the present disclosure, the blood glucose average may be the arithmetic mean of all of the blood glucose measurements taken over the preceding selected period of days, for example, the preceding 15 days. In other embodiments, where multiple blood glucose readings are taken per day, the average blood glucose may be calculated by first determining the arithmetic mean of each day's glucose measurements, and then calculating the arithmetic mean of the daily mean blood glucose values over the selected time interval. However, it will be appreciated that different methods of determining the average blood glucose, over different selected time intervals, may be employed and are intended to be included within the scope of the present disclosure.

To select a best fit model for a given patient's blood glucose data, the average blood glucose, as calculated based on a plurality of different time intervals (for example, 15, 30, 60 and 90 days), are each used in a plurality of different formulas for relating average blood glucose to A1c levels so as to obtain a plurality of calculated A1c levels of the patient. For example, without intending to be limiting, these formulas may include the six different formulas that are described above, obtained from various research papers and medical studies. Table 2 below summarizes the six formulas that are used in an embodiment of the present disclosure; the numbers assigned below to the formulas (eg: Formula 1, Formula 2, etc.) will be used throughout the remainder of this disclosure to refer to each specific formula.

TABLE 2

Formulas for Predicting A1c

| Formula 1 | $A1c = (BG_{avg} + 79.21)/34.74$ |
| Formula 2 | $A1c = (BG_{avg} + 46.7)/28.7$ |
| Formula 3 | $A1c = (BG_{avg} + 36.9)/28.0$ |
| Formula 4 | $A1c = (BG_{avg} + 68.6)/31.5$ |
| Formula 5 | $A1c = (BG_{avg} + 77.3)/35.6$ |
| Formula 6 | $A1c = (BG_{avg} + 86.0)/33.3$ |

Each of the calculated A1c values may then be compared against the one or more measured A1c values that are available for a given patient. By comparing each of the calculated A1c values against each measured A1c value, it may be determined which combination of formula and selected time interval for calculating an average blood glucose results in the least amount of variance between the calculated and measured A1c values. The combination of the selected time interval for the average blood glucose calculation and formula, which results in the lowest amount of variance between the calculated A1c value and the measured A1c value, is identified as the best fit model for the available data set.

As an example of how the selection of a best fit model may occur, using the blood glucose data of a patient provided in Table 7 (appended at the end of the description), and the measured A1c levels of the patient provided in Table 1, Table 3A below shows the average blood glucose calculated over the previous 15 day interval, on each of the dates on which a blood sample was taken for measurement of the patient's A1c levels, and also shows the resulting calculated A1c values as calculated for each of those days, applying each of the six formulas to obtain the plurality of calculated A1c values. In the right-hand column are the actual A1c values, as measured on those dates, and the bottom row provides the average variance between each of the calculated A1c values and measured A1c values for each formula, calculated by taking the arithmetic mean of the absolute value of the variance between each calculated and measured A1c value. Similarly, Tables 3B, 3C and 3D each show the same calculations as performed in Table 3A, but using average blood glucose values calculated over the 30-day, 60-day and 90-day intervals preceding the date on which an A1c measurement was taken, respectively.

TABLE 3A

| Running $BG_{avg}$ 15 Days | | Predicted $A1_c$ | | | | | | Meas. |
|---|---|---|---|---|---|---|---|---|
| Date | $BG_{avg}$ | 1 | 2 | 3 | 4 | 5 | 6 | A1c |
| Jan. 15, 2016 | 157.7414 | 6.8207 | 7.1234 | 6.9515 | 7.1854 | 6.6023 | 7.3196 | 7.4 |
| May 21, 2016 | 188.9512 | 7.7191 | 8.2108 | 8.0661 | 8.1762 | 7.479 | 8.2568 | 8.3 |
| Sep. 17, 2016 | 199.5957 | 8.0255 | 8.5817 | 8.4463 | 8.5142 | 7.778 | 8.5764 | 7.3 |
| Average Variance | | 0.6286 | 0.5492 | 0.6096 | 0.5175 | 0.6989 | 0.4667 | |

TABLE 3B

| Running $BG_{avg}$ 30 Days | | Predicted $A1_c$ | | | | | | Meas. |
|---|---|---|---|---|---|---|---|---|
| Date | $BG_{avg}$ | 1 | 2 | 3 | 4 | 5 | 6 | A1c |
| Jan. 15, 2016 | 166.125 | 7.0620 | 7.4155 | 7.2509 | 7.4516 | 6.8378 | 7.5713 | 7.4 |
| May 21, 2016 | 176.0217 | 7.3469 | 7.7603 | 7.6043 | 7.7658 | 7.1158 | 7.8685 | 8.3 |
| Sep. 17, 2016 | 188.7216 | 7.7125 | 8.2028 | 8.0579 | 8.1689 | 7.4725 | 8.2499 | 7.3 |
| Average Variance | | 0.5679 | 0.4860 | 0.5342 | 0.4849 | 0.6396 | 0.5176 | |

TABLE 3C

| Running $BG_{avg}$ 60 Days | | Predicted $A1_c$ | | | | | | Meas. |
|---|---|---|---|---|---|---|---|---|
| Date | $BG_{avg}$ | 1 | 2 | 3 | 4 | 5 | 6 | A1c |
| Jan. 15, 2016 | 164.9247 | 7.0275 | 7.3737 | 7.2080 | 7.4135 | 6.8041 | 7.5353 | 7.4 |
| May 21, 2016 | 172.0425 | 7.2324 | 7.6217 | 7.4622 | 7.6394 | 7.0040 | 7.7490 | 8.3 |
| Sep. 17, 2016 | 194.4497 | 7.8774 | 8.4024 | 8.2625 | 8.3508 | 7.6334 | 8.4219 | 7.3 |
| Average Variance | | 0.6725 | 0.6023 | 0.6641 | 0.5750 | 0.7418 | 0.6027 | |

TABLE 3D

| Running $BG_{avg}$ 90 Days | | Predicted $A1_c$ | | | | | | Meas. |
|---|---|---|---|---|---|---|---|---|
| Date | $BG_{avg}$ | 1 | 2 | 3 | 4 | 5 | 6 | A1c |
| Jan. 15, 2016 | 167.3476 | 7.0972 | 7.4581 | 7.2946 | 7.4904 | 6.8721 | 7.6080 | 7.4 |
| May 21, 2016 | 167.1881 | 7.0926 | 7.4525 | 7.2889 | 7.4853 | 6.8676 | 7.6032 | 8.3 |
| Sep. 17, 2016 | 197.1956 | 7.9564 | 8.4981 | 8.3606 | 8.4380 | 7.7105 | 8.5044 | 7.3 |
| Average Variance | | 0.7222 | 0.7012 | 0.7257 | 0.6810 | 0.7903 | 0.7031 | |

A model may be defined as a mathematical relationship between a patient's blood glucose measurements taken on a daily basis and the patient's A1c levels. In an embodiment of the present disclosure, the models discussed herein are a combination of a mathematical equation defining the relationship between average blood glucose and A1c, and a selected time interval over which the running blood glucose average will be calculated from the blood glucose measurements collected during that selected time interval. Thus, for example, in an embodiment of the present disclosure, there are four different time intervals for calculating the running blood glucose average, each of which are used in the six formulas to calculate the patient's A1c. In other words, there are twenty-four possible models being tested in the method described herein to identify the best fit model. However, a person skilled in the art will appreciate that the methods described herein are not limited to using the particular six formulas and four time intervals that define the twenty-four possible models, and that combinations of other formulas and/or other time intervals may also be used to define a relationship between a patient's A1c and their average blood glucose, and such alternative models are intended to be included in the scope of the present disclosure.

Once the calculations described above have been run, the best fit model may be determined, in one aspect of the present disclosure, by selecting the model which has the lowest amount of variance between the calculated and measured A1c values. Table 4 below summarizes the average variance values shown in the last row of each of Tables 3A-3D above. As shown in Table 4, in this example, the lowest average variance was obtained using Formula 6 and a 15-day time interval to calculate $BG_{avg}$, and is therefore the identified best fit model for the example provided herein.

TABLE 4

Summary of Average Variances

| Time Interval for $BG_{avg}$ | 1 | 2 | 3 | 4 | 5 | 6 |
|---|---|---|---|---|---|---|
| 15 | 0.6286 | 0.5492 | 0.6096 | 0.5175 | 0.6989 | 0.4667 |
| 30 | 0.5679 | 0.4860 | 0.5342 | 0.4849 | 0.6396 | 0.5176 |
| 60 | 0.6725 | 0.6023 | 0.6641 | 0.5750 | 0.7418 | 0.6027 |
| 90 | 0.7222 | 0.7012 | 0.7257 | 0.6810 | 0.7903 | 0.7031 |

In the example discussed herein, based on a patient's data and having identified the best fit model, in some embodiments of the present disclosure an adjustment factor may also be calculated to account for the average variance between the best fit model and the measured A1c values. In Table 5 below, the model using Formula 6 and the 15-day time interval is applied to predict A1c values, and the arithmetic mean of the variance between the predicted and measured A1c values is calculated to obtain an adjustment factor.

TABLE 5

Adjustment Factor

| Actual A1c | Predicted A1c | Variance |
|---|---|---|
| 7.4 | 7.3196 | 0.0804 |
| 8.3 | 8.2568 | 0.0432 |
| 7.3 | 8.5764 | −1.2764 |
| | Average Variance | −0.3842 |
| | Adjustment Factor (rounded) | −0.38 |

Thus, including the adjustment factor, a best fit model identified for the example discussed above, for predicting the patient's A1c, is:

$$A1c = ((BG_{avg} + 86.0)/33.3) - 0.38$$

wherein, the average blood glucose ($BG_{avg}$) is calculated as the arithmetic mean of all blood glucose measurements taken over the preceding 15 days. Thus, in one aspect of the present disclosure, the patient's predicted A1c would be calculated going forward by applying the identified best fit model to the patient's blood glucose data. The identified best fit model would continue to be used until the results of a new A1c assay become available, at which point the same method described above may be applied to the new data available to identify the best fit model, which may include, in some embodiments, an adjustment factor. In some embodiments, the blood glucose data set of the patient may be updated every time the patient uploads data from their blood glucose meter to the patient's device that is in communication with a cloud-based platform through a network. For example, in some embodiments the blood glucose data set may be updated every two weeks, every five days, every day, or any other frequency as may be appropriate for the patient or as determined by the HCP.

System for Monitoring Effectiveness of a Diabetes Management Program

In some aspects of the present disclosure, a system provides for the transfer of blood glucose data, from one or more patients, to a cloud-based platform, which performs the necessary methods on the collected blood glucose data to predict a patient's A1c values. In another aspect of the present disclosure, the predicted A1c value may be communicated to the patient, the HCP, and any other persons designated or authorized by the patient, thereby providing a measure of the effectiveness of the patient's diabetes management program and an indication of whether changes need to be made. In some embodiments, as will be described below, the system may also provide information about the monitoring of patients and the effectiveness of their diabetes management, including adjustments to the patient's treatment plan by the HCP, to a healthcare payer, which information may be used by the payer to evaluate the performance of HCPs and may also include an incentive system for encouraging better management of the diabetes care for patients.

Referring now to FIG. 1, in an embodiment of the present disclosure, a diabetes care management system 10 may be deployed on a cloud-based platform 20, the cloud-based platform 20 including a server distributed system wherein the servers include one or more databases 30 for storing the data of individual patients, one or more processors 44 performing the computer implemented methods for predicting A1c values and evaluating the predicted A1c values to determine whether escalation of a diabetes care management plan is required, and various communication protocols 50, which allow for the exchange of data between the cloud-based platform 20, and a plurality of devices which may be used by patients, HCPs, and healthcare payers so as to exchange data and information with the cloud-based platform 20 over a network, including but not limited to the internet.

A plurality of patients, represented for example in FIG. 1 as patients A, B and C, may each communicate with the cloud-based platform 20 through one or more devices. For example, patient A may have a blood glucose meter 62, and may also have a smart phone, tablet, computer or other digital processor, collectively device 64, which is configured to communicate with the cloud-based platform 20, such as through software or an application that is loaded onto the device 64. Patient A's blood glucose meter 62 may be used to collect samples of blood from Patient A, for example on a daily basis, sometimes multiple times per day, and the blood glucose meter may have an internal memory device which stores data from the blood glucose readings. Periodically, such as for example once every two weeks, the blood glucose meter 62 may upload the blood glucose data to the patient's device 64, either through a data cord or a wireless connection, such as a Bluetooth connection between meter 62 and device 64, and then the device 64 may upload the blood glucose data to the cloud-based platform 20.

Once the blood glucose data is transferred from patient A's device 64 to the cloud-based platform 20, the blood glucose data may be stored in one or more databases 30. Above described methods may then be performed on the data stored in the one or more databases 30, by one or more processors 40, to predict patient A's A1c levels. Once those methods have been implemented to predict Patient A's A1c levels, the cloud-based platform 20 may then send data or information back to patient A's devices, for example by sending data on the patient's predicted A1c levels to the patient's device 64.

It will be appreciated by persons skilled in the art that there are other options for exchanging blood glucose data between a patient and the cloud-based platform 20 which may work and are intended to be included in the present disclosure. For example, patient B may have a different type of blood glucose meter 66 which is capable not only of collecting blood glucose data and transferring that data to the patient's device 64, but is also be capable of receiving data or information or inputs from device 64 of Patient B. For example, Patient B may be able to program their meter 66 to include the target A1c as agreed to between Patient B and the HCP. As a further alternative, another Patient C may have a blood glucose meter 69 which includes input interfaces allowing the patient to input additional data directly into the blood glucose meter, and which may also include the devices and communication protocols which enable the blood glucose meter 69 to communicate directly with the cloud-based platform 20 so as to exchange data between the blood glucose meter 69 and the cloud-based platform 20 through a network, such as the internet.

In addition, the HCPs, for example HCPs D and E, may also have devices 70, 70 which are capable of exchanging data and information with the cloud-based platform 20. For example, without intending to be limiting, each of HCPs D and E may have devices 70 which may include a general use computer, a smartphone, a tablet or similar devices, which are configured to communicate with the cloud-based platform 20. For example, the HCP devices 70, 70 may include applications or software downloaded onto the device 70 which enables communication between device 70 and the cloud-based platform 20; or in other examples, the device 70 may include internet browser software, enabling access to the cloud-based platform 20 through a secure internet portal. For example, without intending to be limiting, the devices 70 may be used by HCPs D or E to receive and review a patient's blood glucose monitoring data, as well as the patient's most up-to-date predicted and measured A1c levels, and may also provide, for example, alerts indicating whether the patient's data indicates a need for intervention by the HCP or changes to the diabetes management program in order to improve the management of the patient's diabetes. HCPs may also be able to use the devices 70 to schedule follow up appointments with the patient and to input information into the system pertaining to a particular patient, such as revising the target A1c levels or adjusting the escalation criteria by which the system will evaluate the patient's A1c levels and determine whether treatment escalation is required.

As will be further explained below, in some embodiments of the present disclosure, one or more healthcare payers, such as payers F and G, may also have access to some of the data provided by the cloud-based platform 20, allowing the payers F and G to monitor the overall effectiveness of the HCPs in effectively managing the diabetes of their patients. The one or more payers F and G, for example, may include governments, such as in a healthcare system where the government pays for healthcare services on behalf of its citizens, and/or may include insurance companies which may pay for a portion of the diabetes care being received by patients. Payers, also referred to interchangeably herein as insurers, may also include, for example, pharmaceutical companies which may supply diabetes testing supplies and drugs to a particular healthcare system or to certain HCPs or patients within that system. Payers F and G may have general-purpose devices 70, including but not limited to general-purpose computers, tablets or smart phones, which are configured to exchange information and data with the cloud-based platform 20 in a similar manner as described above in relation to the HCP devices 70. However, in some embodiments of the present disclosure, information relating to patients received by the payer devices 70 would be anonymized such that the payers would not be capable of identifying a particular patient based on the information the payers receive from the system 10, in order to protect the confidentiality and privacy of the patients.

Advantageously, in some aspects of the present disclosure, the system 10 may be configured to receive blood glucose data from any blood glucose meters 62, 66, and 69 that are presently in the market or which may become available in the market in the future. The cloud-based platform 20 may be designed to collect data, either directly or indirectly, from the portable blood glucose meters 62, 66, and 69. Thus, advantageously, a patient may be able to use the systems and methods described herein without having to invest in additional equipment such as a specialized blood glucose meter. Further advantageously, the devices 64 which may be used by patient, and the computer or smart phone devices 70 which may be used by the HCPs and the payers or insurers, similarly do not require any type of specialized computer equipment. Such equipment is already widely available and likely already in use by the patients and their HCPs, and therefore no specific investment in specialized equipment is needed in order for the patients and HCPs to deploy this system for the monitoring of a plurality of diabetes patients and the effectiveness of their diabetes management plans.

Method for Monitoring Effectiveness of Diabetes Management Program

In another aspect of the present disclosure, a computer-implemented method, to be utilized in the systems described above, for monitoring the effectiveness of a diabetes management program will now be described, with reference to FIG. 2. A computer implemented method 100 for monitoring the effectiveness of a diabetes management program may be initiated at step 101. At step 103, the method may query whether new measured A1c data is available. In the event that new measured A1c data is available, the method proceeds to step 105, wherein the new measured A1c data is uploaded to a computer performing the method. Referring to FIG. 1, such a computer or device may include, for example, a smartphone or general-purpose computer 64 onto which software has been downloaded to perform the methods described herein, or alternatively, the computer or device may include one or more processors 40 which are part of a cloud-based platform 20. Returning to FIG. 2, once the new measured A1c data has been uploaded, any new blood glucose data, comprising daily blood glucose measurements, are also uploaded to the system at step 107.

As illustrated in box 109, the inputs for predicting a patient's A1c include a plurality of time intervals for calculating the average blood glucose of the patient based on daily blood glucose measurements, and also includes the data obtained from measuring the patient's A1c, such as by an assay test conducted on a blood sample in a lab. The inputs also include the patient's blood glucose data, which may be obtained for example, in a typical case, from self-monitoring by the patient using a blood glucose meter 62, 66 or 69; however, other methods of obtaining the patient's blood glucose data on a frequent basis may also be deployed. The inputs further include a plurality of models for relating the calculated average blood glucose to the patient's A1c values. As described in more detail above, each model of the plurality of models comprises a formula, such as one of the six formulas described above, in combination with a selected time interval of the plurality of time intervals for calculating the average or mean blood glucose of the patient. Additional inputs into the system may further include a target A1c value agreed to between the patient to the HCP, which provides the patient with a measure by which the patient can assess the effectiveness of his or her diabetes management program.

The next step in method 100 may include, at step 111, obtaining a plurality of average blood glucose values. This may be accomplished by using a plurality of time intervals over which to calculate the average blood glucose of a given patient. As was described previously, in one embodiment of the present disclosure, the plurality of time intervals may include 15 days, 30 days, 60 days, and 90 days. However, it will be appreciated by a person skilled in the art that other time intervals may be used and are intended to be included within the scope of the present disclosure.

The plurality of average blood glucose values, calculated in step 111, are applied to each of the plurality of formulas, in step 113, to obtain a plurality of calculated A1c values. For example, in one embodiment of the present disclosure, as described above, each of the four average blood glucose values, which are calculated over the time intervals of 15, 30, 60, and 90 days, may be applied to each of the six formulas described above in order to obtain a total of 24 calculated A1c values. Once the plurality of calculated A1c values has been obtained, at step 115, each calculated A1c value may be compared against the actual measured A1c values so as to identify a best fit model (BFM) for the patient's data. In one embodiment of the present disclosure, as described above, the BFM may be identified by calculating the absolute value of the variance between each calculated A1c value and the corresponding measured A1c value, and then comparing the average absolute value variances to identify which model yields the lowest average variance between the calculated and measured A1c values. This identified model becomes the best fit model for the patient's data, which is used in the rest of the steps of method 100 described below.

At step 117, optionally in some embodiments of the present disclosure, an adjustment factor for the BFM identified in step 115 may be determined. As described above, this may be accomplished for example by calculating an arithmetic mean of the variance between each calculated A1c value and each measured A1c value, where the calculated A1c values are obtained by applying the BFM to the data. Thus, as may be seen in FIG. 2, steps 105 through 117 describe a method for selecting a best fit model when new measured A1c data is available. In some embodiments, these steps may only be followed every time new measured A1c data is available, in order to identify or update a BFM which best correlates to the patient's blood glucose data and measured A1c data.

In the event that no new measured A1c data is available, the method 100 engages in calculating a predicted A1c value by applying the previously identified BFM to the blood glucose data obtained from daily monitoring of the patient's blood glucose. As illustrated in FIG. 2, when the method 100 queries, at step 103, whether new measured A1c data is available and no such data is presently available, the method then proceeds to step 121, wherein any new blood glucose data obtained from monitoring of the patient's blood glucose is uploaded to the system. At step 123, the patient's running blood glucose average is calculated from the newly uploaded blood glucose data, according to the identified BFM. For example, if the identified BFM includes calculating average blood glucose over a 30 day time interval, then the method, at step 123, with obtain the average blood glucose by calculating the arithmetic mean of all blood glucose measurements taken in the preceding 30 days.

At step 125, the BFM, which in some embodiments may include an adjustment factor, may be applied to calculate the patient's predicted A1c for that date. At step 127, therapy escalation rules may be applied to the predicted A1c so as to evaluate the patient's A1c and determine whether an alert for therapy escalation may be required. In one embodiment of the present disclosure, the therapy escalation rules may be based on pre-determined guidelines regarding when a patient's diabetes treatment should be escalated based on the patient's predicted A1c. An example of such guidelines could provide that when a patient's A1c levels are equal to or above 8%, for a period of 30 consecutive days, therapy escalation may be required. In a hypothetical scenario, if the patient's A1c values were at 8% or above for a period of 30 days, and the patient is presently on one non-insulin diabetes therapy, such guidelines would recommend that the patient therapy should be escalated to two non-insulin therapies, or in the alternative, the patient should initiate basal insulin treatment. Table 6 below provides an example of escalation rules or guidelines; however, it will be appreciated by person skilled in the art that these escalation rules may be modified in accordance with an HCP's judgement as to when escalation may be required.

TABLE 6

Therapy Escalation Thresholds

| Predicted A1c Equal to or Above: | For a Period of X Consecutive Days: |
|---|---|
| 7 | 180 |
| 7.5 | 90 |
| 8 | 30 |
| 8.5 | 15 |
| 9 | 0 |

Step 129 of the method queries whether the predicted A1c values exceed the escalation thresholds in accordance with the escalation rules applied at step 127. Returning to the hypothetical example described above, if a patient's A1c values were at 8% or above for a period of 30 consecutive days, then this would indicate that the predicted A1c exceeds the escalation threshold, in which case the method would proceed to step 131 where the predicted A1c and a therapy escalation alert would be outputted to the HCP and the patient. Optionally, without intending to be limiting, the alert may include an automated message which is delivered to, or accessed by, the HCPs device 70, alerting the HCP to the possible need for escalating the diabetes therapy of the patient. A similar automated message may also be sent to the patient.

In some embodiments, either the patient or the HCP, or both, may be prompted by the automated message to arrange for an appointment with the HCP in the near future so that the HCP can review the available data and prescribe an escalation in the diabetes therapy of the patient. In addition or in the alternative, the alert to the HCP and the patient may also include a mechanism of automatically scheduling an appointment for the patient to meet with the HCP and review any adjustments that may be required to the treatment plan. The alert may also take various forms, such as for example a visual indication on the patient's devices 64, or the patient's blood glucose metres 66 or 69, indicating to the patient that therapy escalation is now required. Further optionally, the alert may also include recommendations for specific therapy adjustments, for example, by providing an estimation of the new dosage of insulin that should be incorporated into the treatment plan. These examples of automated messages and alerts described above are not intended to be limiting, and it will be appreciated by person skilled in the art that other forms of alerting the patient and the HCP that therapy escalation is required are intended to be included within the scope of the present disclosure.

In some embodiments of the present disclosure, the alert output to the HCP, at step 131, may further include a suggested modification for the patient's diabetes treatment plan. For example, without intending to be limiting, for patients whose treatment plans include insulin injections, step 131 may include a calculation of a suggested insulin dose adjustment, for example by applying the guidelines and calculations provided for insulin dose adjustment by the American Diabetes Association and the American Association of Clinical Endocrinologists. Such insulin dose adjustment calculations would be based on the patient's blood glucose data, which for example may be uploaded at either steps 107 or 121 of method 100.

Returning to the query step 129 of method 100, in the event that the predicted A1c does not exceed the escalation threshold, the method then proceeds to step 133, at which step the predicted A1c and the target A1c may be outputted to one or more authorized persons, for an example through a visual display on the patient's devices 64, and or on the patient's blood glucose metres 66 or 69. Optionally, the patient's predicted A1c, target A1c, and other data relating to the patient may also be outputted to the HCP, for example in the form of a summary report which may be accessed by the HCP at any time. The patient may also decide to authorize other persons to receive the patient's predicted A1c and other information output by the system 10, such as for example any relatives or friends of the patient, for the purpose of supplying that information to the patient's support network to help encourage the patient to comply with the diabetes treatment plan.

Figure 3:
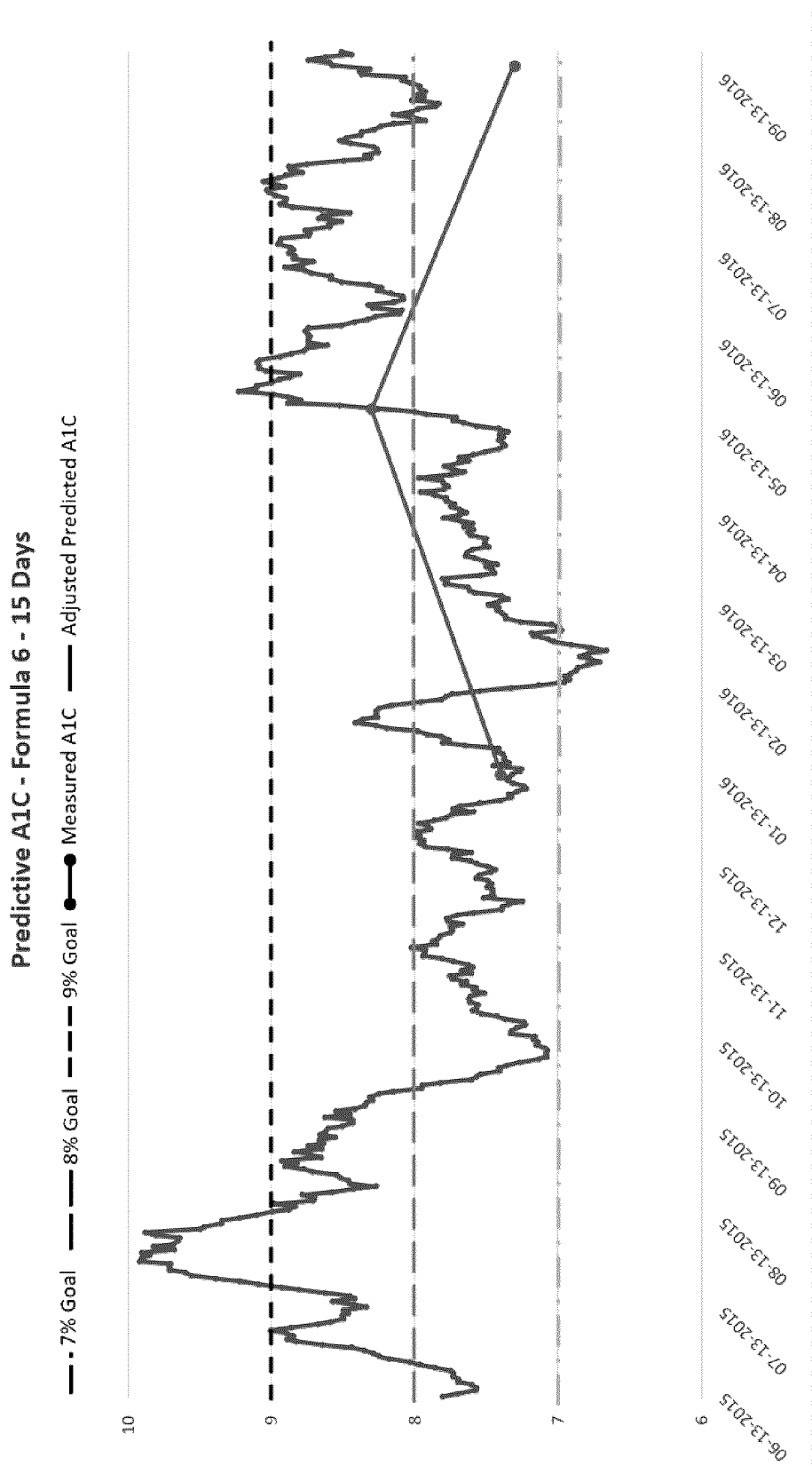
FIG. 3 is a graphical representation of the information output, in an embodiment of the present disclosure.

The output provided at step 133 of the method may also include other types of outputs, such as comparing the predicted A1c to the target A1c in a graphical form, and may also include, for example, a line graph which shows the overall trend of the patient's data over the preceding period comparing the patient's blood glucose data to the predicted A1c data, as well as displaying any available measured A1c values on the same graph. FIG. 3 shows an example of a graph, displaying the data used in the example calculations above, including the adjusted predicted A1c (as calculated from the blood glucose data) and the measured A1c values. Other variations of visual displays and data output to the patient's devices are also intended to be included in the scope of the present disclosure, and the particular outputs described above are not intended to be limiting.

Figure 2:
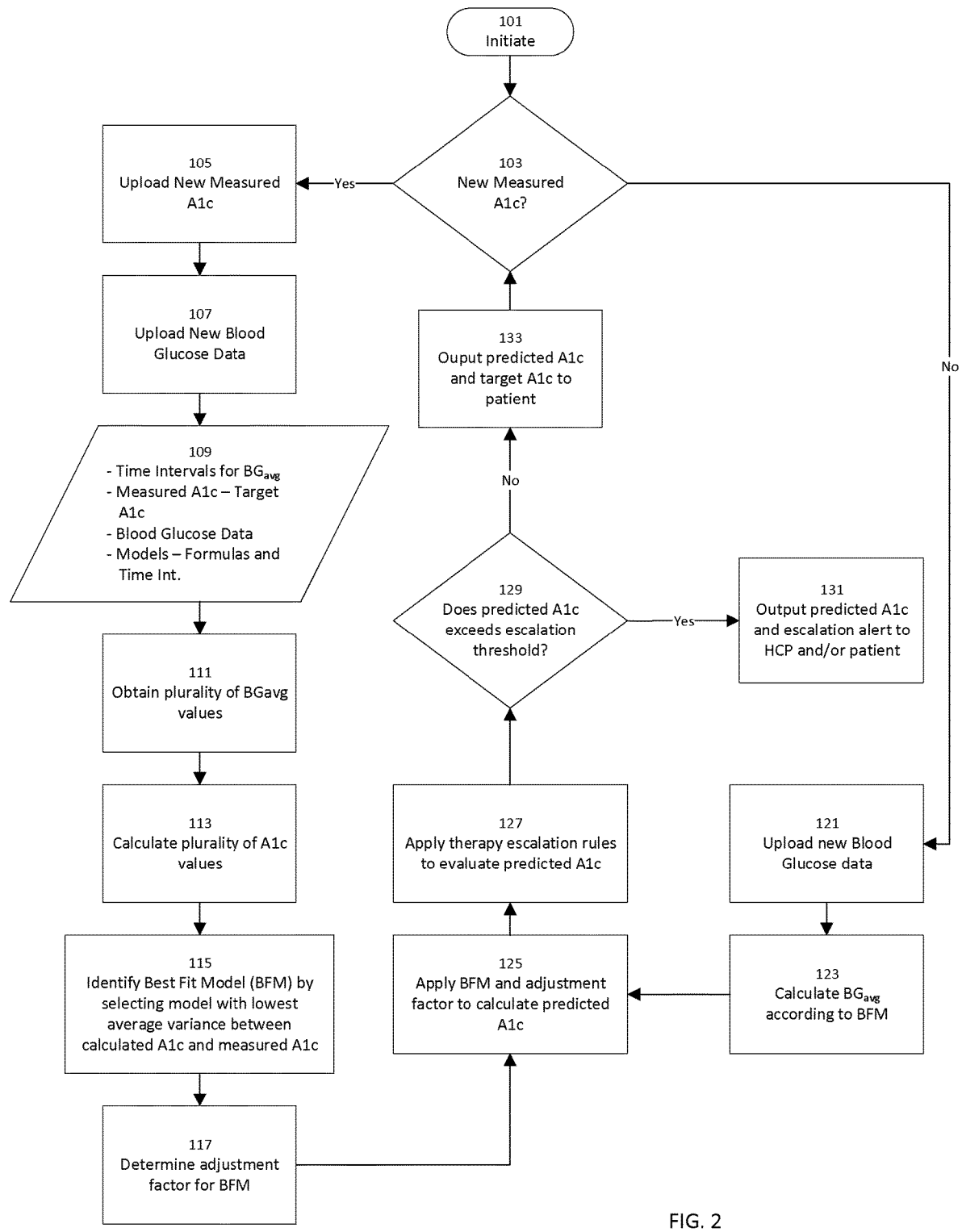
FIG. 2 is a logic flow chart of a computer-implemented method for monitoring the effectiveness of a patient's diabetes treatment, in an embodiment of the present disclosure.

As shown in FIG. 2, steps 121 through 133 may be repeated every time new blood glucose data becomes available, for example every two weeks, every five days, every day, or any other frequency as determined appropriate by the HCP and the patient, or as may be deemed appropriate for the system 10. This loop of the method, including steps 121 through 133, may be repeated until new measured A1c data becomes available, in which case steps 105 through 117 are followed in order to identify a new BFM. In this manner, the BFM may be continually updated based on measured values of A1c, whenever they become available, which may increase the accuracy of the predicted A1c calculated by method 100.

TABLE 7

| BG Data Set | | |
|---|---|---|
| #Days | Date | BG |
| — | Sep. 22, 2016 | 342 |
| — | Sep. 22, 2016 | 207 |
| — | Sep. 22, 2016 | 202 |
| 1 | Sep. 21, 2016 | 148 |
| 1 | Sep. 21, 2016 | 232 |
| 1 | Sep. 21, 2016 | 268 |
| 1 | Sep. 21, 2016 | 250 |
| 1 | Sep. 21, 2016 | 256 |
| 1 | Sep. 21, 2016 | 77 |
| 2 | Sep. 20, 2016 | 221 |
| 2 | Sep. 20, 2016 | 283 |
| 2 | Sep. 20, 2016 | 85 |
| 2 | Sep. 20, 2016 | 86 |
| 2 | Sep. 20, 2016 | 227 |
| 3 | Sep. 19, 2016 | 286 |
| 3 | Sep. 19, 2016 | 137 |
| 3 | Sep. 19, 2016 | 184 |
| 3 | Sep. 19, 2016 | 173 |
| 4 | Sep. 18, 2016 | 220 |
| 4 | Sep. 18, 2016 | 239 |
| 5 | Sep. 17, 2016 | 189 |
| 5 | Sep. 17, 2016 | 169 |
| 5 | Sep. 17, 2016 | 223 |
| 6 | Sep. 16, 2016 | 236 |
| 6 | Sep. 16, 2016 | 167 |
| 7 | Sep. 15, 2016 | 295 |
| 7 | Sep. 15, 2016 | 256 |
| 7 | Sep. 15, 2016 | 158 |
| 8 | Sep. 14, 2016 | 297 |
| 8 | Sep. 14, 2016 | 261 |
| 8 | Sep. 14, 2016 | 198 |
| 8 | Sep. 14, 2016 | 148 |
| 9 | Sep. 13, 2016 | 220 |
| 9 | Sep. 13, 2016 | 184 |
| 9 | Sep. 13, 2016 | 137 |
| 10 | Sep. 12, 2016 | 160 |
| 10 | Sep. 12, 2016 | 171 |
| 10 | Sep. 12, 2016 | 166 |
| 11 | Sep. 11, 2016 | 275 |
| 11 | Sep. 11, 2016 | 81 |
| 12 | Sep. 10, 2016 | 175 |
| 12 | Sep. 10, 2016 | 166 |
| 12 | Sep. 10, 2016 | 205 |
| 12 | Sep. 10, 2016 | 128 |
| 12 | Sep. 10, 2016 | 184 |

TABLE 7-continued

BG Data Set

| #Days | Date | BG |
|---|---|---|
| 13 | Sep. 9, 2016 | 137 |
| 13 | Sep. 9, 2016 | 158 |
| 14 | Sep. 8, 2016 | 153 |
| 14 | Sep. 8, 2016 | 243 |
| 14 | Sep. 8, 2016 | 185 |
| 14 | Sep. 8, 2016 | 207 |
| 15 | Sep. 7, 2016 | 187 |
| 15 | Sep. 7, 2016 | 229 |
| 16 | Sep. 6, 2016 | 236 |
| 16 | Sep. 6, 2016 | 218 |
| 16 | Sep. 6, 2016 | 167 |
| 17 | Sep. 5, 2016 | 288 |
| 17 | Sep. 5, 2016 | 248 |
| 17 | Sep. 5, 2016 | 293 |
| 17 | Sep. 5, 2016 | 293 |
| 17 | Sep. 5, 2016 | 227 |
| 18 | Sep. 4, 2016 | 284 |
| 18 | Sep. 4, 2016 | 211 |
| 19 | Sep. 3, 2016 | 148 |
| 19 | Sep. 3, 2016 | 76 |
| 19 | Sep. 3, 2016 | 112 |
| 20 | Sep. 2, 2016 | 232 |
| 21 | Sep. 1, 2016 | 63 |
| 21 | Sep. 1, 2016 | 148 |
| 21 | Sep. 1, 2016 | 97 |
| 21 | Sep. 1, 2016 | 128 |
| 21 | Sep. 1, 2016 | 115 |
| 22 | Aug. 31, 2016 | 220 |
| 22 | Aug. 31, 2016 | 268 |
| 22 | Aug. 31, 2016 | 229 |
| 22 | Aug. 31, 2016 | 196 |
| 23 | Aug. 30, 2016 | 223 |
| 23 | Aug. 30, 2016 | 193 |
| 23 | Aug. 30, 2016 | 252 |
| 23 | Aug. 30, 2016 | 205 |
| 24 | Aug. 29, 2016 | 43 |
| 24 | Aug. 29, 2016 | 49 |
| 24 | Aug. 29, 2016 | 162 |
| 24 | Aug. 29, 2016 | 124 |
| 25 | Aug. 28, 2016 | 194 |
| 25 | Aug. 28, 2016 | 157 |
| 25 | Aug. 28, 2016 | 182 |
| 25 | Aug. 28, 2016 | 229 |
| 26 | Aug. 27, 2016 | 126 |
| 26 | Aug. 27, 2016 | 88 |
| 27 | Aug. 26, 2016 | 106 |
| 27 | Aug. 26, 2016 | 160 |
| 27 | Aug. 26, 2016 | 149 |
| 28 | Aug. 25, 2016 | 194 |
| 28 | Aug. 25, 2016 | 130 |
| 29 | Aug. 24, 2016 | 185 |
| 29 | Aug. 24, 2016 | 128 |
| 29 | Aug. 24, 2016 | 169 |
| 29 | Aug. 24, 2016 | 104 |
| 30 | Aug. 23, 2016 | 189 |
| 30 | Aug. 23, 2016 | 232 |
| 30 | Aug. 23, 2016 | 227 |
| 30 | Aug. 23, 2016 | 221 |
| 31 | Aug. 22, 2016 | 268 |
| 31 | Aug. 22, 2016 | 166 |
| 31 | Aug. 22, 2016 | 101 |
| 32 | Aug. 21, 2016 | 245 |
| 32 | Aug. 21, 2016 | 133 |
| 32 | Aug. 21, 2016 | 256 |
| 32 | Aug. 21, 2016 | 315 |
| 33 | Aug. 20, 2016 | 284 |
| 33 | Aug. 20, 2016 | 202 |
| 34 | Aug. 19, 2016 | 317 |
| 34 | Aug. 19, 2016 | 214 |
| 35 | Aug. 18, 2016 | 175 |
| 35 | Aug. 18, 2016 | 175 |
| 35 | Aug. 18, 2016 | 189 |
| 36 | Aug. 17, 2016 | 223 |
| 36 | Aug. 17, 2016 | 288 |
| 36 | Aug. 17, 2016 | 196 |
| 36 | Aug. 17, 2016 | 157 |
| 37 | Aug. 16, 2016 | 106 |
| 37 | Aug. 16, 2016 | 137 |
| 37 | Aug. 16, 2016 | 158 |
| 38 | Aug. 15, 2016 | 220 |
| 38 | Aug. 15, 2016 | 105 |
| 38 | Aug. 15, 2016 | 228 |
| 38 | Aug. 15, 2016 | 124 |
| 39 | Aug. 14, 2016 | 191 |
| 39 | Aug. 14, 2016 | 201 |
| 39 | Aug. 14, 2016 | 156 |
| 40 | Aug. 13, 2016 | 207 |
| 40 | Aug. 13, 2016 | 174 |
| 41 | Aug. 12, 2016 | 210 |
| 41 | Aug. 12, 2016 | 241 |
| 41 | Aug. 12, 2016 | 216 |
| 41 | Aug. 12, 2016 | 246 |
| 42 | Aug. 11, 2016 | 225 |
| 42 | Aug. 11, 2016 | 157 |
| 42 | Aug. 11, 2016 | 135 |
| 42 | Aug. 11, 2016 | 143 |
| 43 | Aug. 10, 2016 | 213 |
| 43 | Aug. 10, 2016 | 239 |
| 43 | Aug. 10, 2016 | 111 |
| 44 | Aug. 9, 2016 | 236 |
| 44 | Aug. 9, 2016 | 166 |
| 44 | Aug. 9, 2016 | 124 |
| 45 | Aug. 8, 2016 | 237 |
| 45 | Aug. 8, 2016 | 138 |
| 46 | Aug. 7, 2016 | 249 |
| 46 | Aug. 7, 2016 | 270 |
| 46 | Aug. 7, 2016 | 230 |
| 47 | Aug. 6, 2016 | 192 |
| 47 | Aug. 6, 2016 | 154 |
| 47 | Aug. 6, 2016 | 61 |
| 48 | Aug. 5, 2016 | 155 |
| 48 | Aug. 5, 2016 | 106 |
| 48 | Aug. 5, 2016 | 238 |
| 49 | Aug. 4, 2016 | 274 |
| 49 | Aug. 4, 2016 | 177 |
| 50 | Aug. 3, 2016 | 204 |
| 50 | Aug. 3, 2016 | 128 |
| 50 | Aug. 3, 2016 | 265 |
| 50 | Aug. 3, 2016 | 284 |
| 50 | Aug. 3, 2016 | 204 |
| 51 | Aug. 2, 2016 | 296 |
| 51 | Aug. 2, 2016 | 285 |
| 51 | Aug. 2, 2016 | 194 |
| 51 | Aug. 2, 2016 | 108 |
| 52 | Aug. 1, 2016 | 277 |
| 52 | Aug. 1, 2016 | 125 |
| 52 | Aug. 1, 2016 | 205 |
| 53 | Jul. 31, 2016 | 292 |
| 53 | Jul. 31, 2016 | 231 |
| 54 | Jul. 30, 2016 | 280 |
| 54 | Jul. 30, 2016 | 272 |
| 54 | Jul. 30, 2016 | 278 |
| 54 | Jul. 30, 2016 | 188 |
| 54 | Jul. 30, 2016 | 295 |
| 55 | Jul. 29, 2016 | 233 |
| 55 | Jul. 29, 2016 | 223 |
| 55 | Jul. 29, 2016 | 267 |
| 55 | Jul. 29, 2016 | 252 |
| 56 | Jul. 28, 2016 | 230 |
| 56 | Jul. 28, 2016 | 190 |
| 56 | Jul. 28, 2016 | 153 |
| 57 | Jul. 27, 2016 | 186 |
| 57 | Jul. 27, 2016 | 194 |
| 57 | Jul. 27, 2016 | 194 |
| 57 | Jul. 27, 2016 | 187 |
| 58 | Jul. 26, 2016 | 192 |
| 58 | Jul. 26, 2016 | 257 |
| 59 | Jul. 25, 2016 | 165 |
| 59 | Jul. 25, 2016 | 248 |
| 59 | Jul. 25, 2016 | 228 |
| 60 | Jul. 24, 2016 | 279 |
| 60 | Jul. 24, 2016 | 215 |

TABLE 7-continued

BG Data Set

| #Days | Date | BG |
|---|---|---|
| 61 | Jul. 23, 2016 | 210 |
| 61 | Jul. 23, 2016 | 262 |
| 61 | Jul. 23, 2016 | 69 |
| 61 | Jul. 23, 2016 | 151 |
| 62 | Jul. 22, 2016 | 213 |
| 62 | Jul. 22, 2016 | 180 |
| 63 | Jul. 21, 2016 | 189 |
| 64 | Jul. 20, 2016 | 125 |
| 64 | Jul. 20, 2016 | 203 |
| 64 | Jul. 20, 2016 | 141 |
| 65 | Jul. 19, 2016 | 203 |
| 65 | Jul. 19, 2016 | 181 |
| 66 | Jul. 18, 2016 | 211 |
| 66 | Jul. 18, 2016 | 205 |
| 66 | Jul. 18, 2016 | 167 |
| 66 | Jul. 18, 2016 | 166 |
| 67 | Jul. 17, 2016 | 204 |
| 67 | Jul. 17, 2016 | 265 |
| 68 | Jul. 16, 2016 | 267 |
| 68 | Jul. 16, 2016 | 192 |
| 69 | Jul. 15, 2016 | 182 |
| 70 | Jul. 14, 2016 | 256 |
| 70 | Jul. 14, 2016 | 250 |
| 70 | Jul. 14, 2016 | 133 |
| 70 | Jul. 14, 2016 | 178 |
| 71 | Jul. 13, 2016 | 126 |
| 71 | Jul. 13, 2016 | 58 |
| 71 | Jul. 13, 2016 | 169 |
| 71 | Jul. 13, 2016 | 304 |
| 71 | Jul. 13, 2016 | 282 |
| 71 | Jul. 13, 2016 | 139 |
| 72 | Jul. 12, 2016 | 212 |
| 72 | Jul. 12, 2016 | 300 |
| 72 | Jul. 12, 2016 | 249 |
| 72 | Jul. 12, 2016 | 301 |
| 73 | Jul. 11, 2016 | 220 |
| 73 | Jul. 11, 2016 | 178 |
| 73 | Jul. 11, 2016 | 203 |
| 74 | Jul. 10, 2016 | 189 |
| 74 | Jul. 10, 2016 | 109 |
| 74 | Jul. 10, 2016 | 108 |
| 75 | Jul. 9, 2016 | 261 |
| 75 | Jul. 9, 2016 | 279 |
| 75 | Jul. 9, 2016 | 236 |
| 76 | Jul. 8, 2016 | 172 |
| 76 | Jul. 8, 2016 | 277 |
| 76 | Jul. 8, 2016 | 233 |
| 77 | Jul. 7, 2016 | 338 |
| 77 | Jul. 7, 2016 | 211 |
| 78 | Jul. 6, 2016 | 217 |
| 78 | Jul. 6, 2016 | 140 |
| 78 | Jul. 6, 2016 | 191 |
| 79 | Jul. 5, 2016 | 219 |
| 79 | Jul. 5, 2016 | 195 |
| 80 | Jul. 4, 2016 | 225 |
| 80 | Jul. 4, 2016 | 409 |
| 80 | Jul. 4, 2016 | 173 |
| 80 | Jul. 4, 2016 | 174 |
| 81 | Jul. 3, 2016 | 275 |
| 81 | Jul. 3, 2016 | 191 |
| 81 | Jul. 3, 2016 | 138 |
| 82 | Jul. 2, 2016 | 237 |
| 82 | Jul. 2, 2016 | 184 |
| 82 | Jul. 2, 2016 | 146 |
| 83 | Jul. 1, 2016 | 172 |
| 83 | Jul. 1, 2016 | 165 |
| 83 | Jul. 1, 2016 | 194 |
| 84 | Jun. 30, 2016 | 248 |
| 84 | Jun. 30, 2016 | 209 |
| 84 | Jun. 30, 2016 | 174 |
| 85 | Jun. 29, 2016 | 226 |
| 85 | Jun. 29, 2016 | 217 |
| 85 | Jun. 29, 2016 | 218 |
| 86 | Jun. 28, 2016 | 135 |
| 86 | Jun. 28, 2016 | 185 |
| 87 | Jun. 27, 2016 | 169 |
| 87 | Jun. 27, 2016 | 155 |
| 87 | Jun. 27, 2016 | 148 |
| 88 | Jun. 26, 2016 | 273 |
| 88 | Jun. 26, 2016 | 188 |
| 88 | Jun. 26, 2016 | 184 |
| 89 | Jun. 25, 2016 | 301 |
| 89 | Jun. 25, 2016 | 209 |
| 90 | Jun. 24, 2016 | 196 |
| 90 | Jun. 24, 2016 | 185 |

What is claimed is:

1. A method for monitoring a patient's diabetes treatment plan by predicting the patient's glycated hemoglobin (A1c) based on the patient's blood glucose (BG), the method implemented by a patient device, the patient device having a processor and a tangible memory, the method consisting of:
applying a plurality of A1c models to a BG data set of the patient so as to obtain a corresponding plurality of calculated A1c values, wherein each A1c model of the plurality of A1c models comprises:
a formula selected from a plurality of formulas, the formula correlating a mean BG value to a calculated A1c value of the plurality of A1c values, and wherein the mean BG value is calculated from the BG data set based on a time interval selected from a plurality of time intervals,
identifying a best fit model amongst the plurality of A1c models by evaluating the plurality of calculated A1c values against at least one measured A1c value of the patient,
measuring, by a BG device, a blood sample of the patient to generate at least one new BG data point,
obtaining an updated BG data set from the BG device, the updated BG data set comprising the at least one new BG data point measured by the BG device,
calculating a predicted A1c value by applying the identified best fit model to the updated BG data set,
evaluating the predicted A1c value against a set of escalation rules to determine whether an escalation alert is required,
alerting the patient's healthcare provider when it is determined the escalation alert is required, and
providing a modification for the patient's diabetes treatment plan,
wherein the patient device monitors overall effectiveness of the patient's diabetes treatment plan at controlling a diabetes condition of the patient by monitoring changes in the predicted A1c value.

2. The method of claim 1, further comprising the step of:
outputting the predicted A1c value to one or more authorized persons.

3. The method of claim 1 wherein the step of identifying the best fit model further includes determining an adjustment factor so as to adjust the best fit model to better correlate with the patient's BG data set, and
wherein the step of calculating the predicted A1c value further includes applying the adjustment factor to the best fit model.

4. The method of claim 1 wherein the plurality of formulas is selected from the group consisting of: A1c=($BG_{avg}$+

79.21)/34.74, A1c=($BG_{avg}$+46.7)/28.7, A1c=($BG_{avg}$+36.9)/28.0, A1c=($BG_{avg}$+68.6)/31.5, and A1c=($BG_{avg}$+77.3)/35.6, A1c=($BG_{avg}$+86.0)/33.3.

5. The method of claim 4 wherein the plurality of time intervals is selected from a group consisting of: 15 days, 30 days, 60 days, and 90 days.

6. The method of claim 2 wherein the one or more authorized persons are selected from a group consisting of: the patient, the patient's health care provider, an insurer of the patient, a friend of the patient, and a family member of the patient.

7. The method of claim 2 wherein the step of outputting the predicted A1c value includes outputting a visual display having a plurality of elements, the plurality of elements selected from a group consisting of: a graph plotting a plurality of predicted A1c values over time, a graph plotting the BG data set over time, a graph plotting the at least one measured A1c value over time, a visual indicator representing the predicted A1c value against a target A1c value, and a visual indicator representing a most recent measured A1c value of the at least one measured A1c value.

8. The method of claim 7 wherein the graph plotting a plurality of predicted A1c values over time, the graph plotting the BG data set over time and the graph plotting the at least one measured A1c value over time are combined into a single graph.

9. The method of claim 1 wherein the step of alerting the patient's healthcare provider further includes scheduling an appointment for the patient with the healthcare provider.

10. The method of claim 1 wherein the modification for the patient's diabetes treatment plan includes a calculation of an adjusted insulin dosage for the patient.

11. The method of claim 1 wherein the steps of applying a plurality of A1c models to a BG data set of the patient and identifying a best fit model amongst the plurality of A1c models only occur when the at least one measured A1c value includes at least one measured A1c value not previously evaluated.

12. The method of claim 2 wherein the steps of calculating the predicted A1c value, evaluating the predicted A1c value, alerting the patient's healthcare provider and outputting the predicted A1c value occur when new BG data is added to the updated BG data set.

13. The method of claim 12 wherein the new BG data is added to the updated BG data set at a frequency selected from the group consisting of: once every two weeks, once every five days, and once every day.

14. A system for monitoring a patient's diabetes treatment plan by predicting the patient's glycated hemoglobin (A1c) based on the patient's blood glucose (BG), predicted according to the method of claim 1, the system comprising:
a cloud-based platform including a plurality of servers, the cloud-based platform configured to communicate with a plurality of devices through a network,
the plurality of devices including at least the patient device and a healthcare provider device, wherein the cloud-based platform is configured to receive BG data of the patient.

15. The system of claim 14 wherein the plurality of devices further includes a payer device configured to communicate with the cloud-based platform.

16. The system of claim 14 wherein the system is configured to monitor a diabetes treatment plan of each patient of a plurality of patients.

17. The system of claim 14 wherein the plurality of devices is selected from a group consisting of: computers, smart phones, desktop computers, laptop computers, tablets and BG devices.

18. The method of claim 1, wherein the BG device is selected from a group consisting of: a BG meter and a continuous blood glucose monitoring device.

19. The method of claim 1, wherein the patient device is selected from a group consisting of: the BG device, a computer, a smart phone, a desktop computer, a laptop computer, and a tablet.

20. A method for monitoring a patient's diabetes treatment plan by predicting the patient's glycated hemoglobin (A1c) based on the patient's blood glucose (BG), the method implemented by a patient device, the patient device having a processor and a tangible memory, the method consisting of:
applying a plurality of A1c models to a BG data set of the patient so as to obtain a corresponding plurality of calculated A1c values, wherein each A1c model of the plurality of A1c models comprises:
a formula selected from a plurality of formulas, the formula correlating a mean BG value to a calculated A1c value of the plurality of A1c values, and wherein the mean BG value is calculated from the BG data set based on a time interval selected from a plurality of time intervals,
identifying a best fit model amongst the plurality of A1c models by evaluating the plurality of calculated A1c values against at least one measured A1c value of the patient,
measuring, by a BG device, a blood sample of the patient to generate at least one new BG data point,
obtaining an updated BG data set from the BG data device, the updated BG data set comprising the at least one new BG data point measured by the BG device,
calculating a predicted A1c value by applying the identified best fit model to the updated BG data set,
evaluating the predicted A1c value against a set of escalation rules to determine whether an escalation of the patient's diabetes treatment plan is required, and
escalating the patient's diabetes treatment plan if the evaluating step determines the escalation of the patient's diabetes treatment plan is required.

21. The method of claim 20 wherein the step of escalating the patient's diabetes treatment plan includes adjusting an insulin dosage of the patient.

22. The method of claim 20 wherein the step of identifying the best fit model further includes determining an adjustment factor to adjust the best fit model to better correlate with the patient's BG data set, and
wherein the step of calculating the predicted A1c value further includes applying the adjustment factor to the best fit model.

23. The method of claim 20 wherein the plurality of formulas is selected from the group consisting of: A1c=($BG_{avg}$+79.21)/34.74, A1c=($BG_{avg}$+46.7)/28.7, A1c=($BG_{avg}$+36.9)/28.0, A1c=($BG_{avg}$+68.6)/31.5, and A1c=($BG_{avg}$+77.3)/35.6, A1c=($BG_{avg}$+86.0)/33.3.

24. The method of claim 23 wherein the plurality of time intervals is selected from a group consisting of: 15 days, 30 days, 60 days, and 90 days.

25. The method of claim 20 wherein the steps of applying a plurality of A1c models to a BG data set of the patient and identifying a best fit model amongst the plurality of A1c models only occur when the at least one measured A1c value includes at least one measured A1c value not previously evaluated.

26. The method of claim 20 wherein the steps of calculating the predicted A1c value, evaluating the predicted A1c value and escalating the patient's diabetes treatment plan occur when new BG data is added to the updated BG data set.

27. The method of claim 26 wherein the new BG data is added to the updated BG data set at a frequency selected from the group consisting of: once every two weeks, once every five days, and once every day.

28. A system for monitoring a patient's diabetes treatment plan by predicting the patient's glycated hemoglobin (A1c) based on the patient's blood glucose (BG), predicted according to the method of claim 20, the system comprising:
   a cloud-based platform including a plurality of servers, the cloud-based platform configured to communicate with a plurality of devices through a network,
   the plurality of devices including at least the patient device and a healthcare provider device, wherein the cloud-based platform is configured to receive BG data of the patient.

\* \* \* \* \*